(12) United States Patent
Samara et al.

(10) Patent No.: US 7,013,032 B1
(45) Date of Patent: Mar. 14, 2006

(54) METHOD AND APPARATUS FOR SECONDARY CAPTURE OF 3D BASED IMAGES ON A PICTURE ARCHIVAL AND COMMUNICATIONS (PACS) SYSTEM

(75) Inventors: Yaseen Samara, Arlington Heights, IL (US); William M. Stoval, Mt. Prospect, IL (US); Neil D. D'Souza, Mt. Prospect, IL (US); Rahul Choudhury, Mt. Prospect, IL (US); Greg J. Angst, Delafield, WI (US); David W. Kurzynski, Vernon Hills, IL (US); Jerome Knoplioch, Neuilly sur Seine (FR)

(73) Assignee: The General Electric Company, Schenectady, NY (US)

( * ) Notice: Subject to any disclaimer, the term of this patent is extended or adjusted under 35 U.S.C. 154(b) by 0 days.

(21) Appl. No.: 09/449,215

(22) Filed: Nov. 24, 1999

(51) Int. Cl.
 *G06K 9/00* (2006.01)
(52) U.S. Cl. ............... 382/128; 382/305; 128/922; 345/419; 707/10
(58) Field of Classification Search .............. 382/128, 382/154; 345/419–427; 356/12; 128/922
See application file for complete search history.

(56) References Cited

U.S. PATENT DOCUMENTS

| 4,835,688 | A | * | 5/1989 | Kimura ........................ 345/424 |
| 5,226,113 | A | * | 7/1993 | Cline et al. .................. 345/419 |
| 5,537,127 | A | | 7/1996 | Jingu |
| 5,668,846 | A | * | 9/1997 | Fox et al. ........................ 378/4 |
| 5,675,744 | A | | 10/1997 | Tsujii |
| 5,715,823 | A | * | 2/1998 | Wood et al. .................. 128/904 |
| 5,734,915 | A | | 3/1998 | Roewer |
| 5,779,634 | A | | 7/1998 | Ema et al. |
| 5,812,691 | A | * | 9/1998 | Udupa et al. ............... 382/128 |
| 5,835,618 | A | | 11/1998 | Fang et al. |
| 5,835,735 | A | | 11/1998 | Mason et al. |
| 5,915,242 | A | | 6/1999 | Tsujii |
| 5,930,327 | A | | 7/1999 | Lin |
| 5,959,678 | A | | 9/1999 | Callahan et al. |
| 6,206,566 | B1 | * | 3/2001 | Schuetz ........................ 378/205 |
| 6,370,413 | B1 | * | 4/2002 | Alvarez et al. .............. 128/916 |
| 6,440,071 | B1 | * | 8/2002 | Slayton et al. .............. 128/916 |
| 6,511,426 | B1 | * | 1/2003 | Hossack et al. ............. 600/437 |
| 6,718,192 | B1 | * | 4/2004 | Samara et al. .............. 600/407 |

OTHER PUBLICATIONS

Sun et al. "Feature-based Interactive Visualization of Volumetric Medical Data" IEEE 1998.*

(Continued)

*Primary Examiner*—Samir Ahmed
*Assistant Examiner*—Charles Kim
(74) *Attorney, Agent, or Firm*—Andrus, Sceales, Starke & Sawall

(57) ABSTRACT

An image management system (10), includes a PACS system. The PACS system (10) includes a PACS server (20) coupled to a communications network (22) and a plurality of PACS workstations (40) also coupled to a communications network (22). Each PACS workstation (40) is configured to receive two dimensional image information and produce a three dimensional image rendering on the PACS workstation (40). The three dimensional image rendering is communicated to the PACS server (20) for storage and later retrieval.

23 Claims, 2 Drawing Sheets

OTHER PUBLICATIONS

Nelson et al. "Visualization of 3D Ultrasound Data" IEEE Computer Graphics & Applications 1993.*

Concurrent Processing for Picture Archiving and Communication System (PACS) by Chong et al., Proceedings of IEEE Singapore International Conference 1995, pp. 468-472.*

"PACS: Basic Principles and Applications" by Huang. Wiley-Liss; 1 edition, Nov. 20, 1998. pp. 177-231, 269-288, 305-342.*

Siemens, Clinical Networking—copies of web pages found at http://www.med.siemens.com as of Oct. 20, 1999.

* cited by examiner

METHOD AND APPARATUS FOR SECONDARY CAPTURE OF 3D BASED IMAGES ON A PICTURE ARCHIVAL AND COMMUNICATIONS (PACS) SYSTEM

This invention relates to image management systems, and more particularly to image reconstruction on an image workstation coupled to an image manager.

BACKGROUND OF THE INVENTION

Medical scanners and medical imaging machines are an integral part of modern medical practice. These scanners and medical imaging devices utilize both electromagnetic radiation and sonic wave to produce images which are viewed by doctors for the diagnosis and care of patients. For example, ultrasound machines are useful for viewing fetuses during prenatal care in a pregnancy or blood flow patterns in arteries. Magnetic resonance imaging (MRI) machines are useful for producing images of a wide range of soft tissues.

In a large hospital, medical scanners and medical imaging devices are preferably networked with a central image management system, such as a picture archival and communications system (PACS). The PACS is designed to provide a central storage for archive for medical images. Further, PACS is configured so that stored images may be retrieved. Typically, a hospital will have a single PACS that is networked with a plurality of medical scanners and medical imaging devices located throughout the hospital. Further, the PACS will be networked with a plurality of image workstations, such as a PACS workstation. Images generated by medical scanners and medical imaging devices are transferred to the PACS for storage and later retrieval and review by doctors located throughout the hospital at any of the plurality of image workstations.

Conventionally, doctors or users of image workstations (e.g., PACS workstations) were able to view only two dimensional image renderings of the images retrieved from the PACS. Three dimensional image rendering was restricted to three dimensional rendering on stand alone workstations dedicated for three dimensional graphics processing. Further, because of the restriction to stand alone workstations, conventional three dimensional graphics processing was not carried out on PACS workstation therefore image information and data could not be simply received from the PACS server. Further, because the 3D processing is conventionally carried out on stand alone workstations, the PACS has not been used to store 3D image information.

Therefore, there is a need for an image workstation that is in communication with the PACS server and is configured to carry out 3D processing thereon. Further, there is a need for an image workstation that is capable of receiving image information from the PACS server and constructing a 3D image rendering, and communicating the 3D image rendering (or 3D image rendering parameters) to the PACS server for storage and later retrieval.

SUMMARY OF THE INVENTION

A preferred embodiment of the invention relates to an image management system. The image management system includes an image manager having a plurality of inputs and outputs. The inputs are configured to receive image information signals and the outputs configured to provide image output signals. The image manager is configured to store information representative of a plurality of two dimensional image slices and the output signals are representative of the stored two dimensional image slices. The image management system also includes an imaging device having an output coupled to at least one of the inputs of the image manager and is configured to provide an image signal. The image management system further includes an image workstation having an input coupled to at least one of the outputs of the image manager and is configured to receive output signals from the image manager representative of selected two dimensional image slices stored by the image manager. The image workstation is configured to construct three dimensional image renderings from the two dimensional image slices. The image workstation has an output coupled to the image manager. The image workstation is configured to provide the image manager with a signal representative of the three dimensional rendering.

Another embodiment of the invention relates to a method of producing a rendering of a three dimensional object from a plurality of two dimensional image information files. The method includes receiving, by an image manager, a plurality of two dimensional image information files from an imaging device and storing a plurality of two dimensional image files on the image manager. The method also includes communicating selected two dimensional image information files to an image workstation and receiving a two dimensional image information file by the image workstation. The method further includes constructing a three dimensional image file based on the two dimensional image information files and communicating the three dimensional image information file to the image manager.

Yet another embodiment of the invention relates to a medical imaging system. The medical imaging system includes a medical scanner and an image manager coupled to the medical scanner and configured to receive and store signals representative of two dimensional image slices from the medical scanner. The medical imaging system includes an image workstation configured to receive selected signals representative of two dimensional image slices and configured to construct a three dimensional rendering file from the signals representative of the two dimensional image slices. The three dimensional rendering file is communicated to and stored by the image manager.

BRIEF DESCRIPTION OF THE DRAWINGS

The invention will become more fully understood from the following detailed description, taken in conjunction with the accompanying drawings, wherein like reference numerals refer to like parts, in which.

DETAILED DESCRIPTION OF THE PREFERRED EMBODIMENTS

Figure 1:
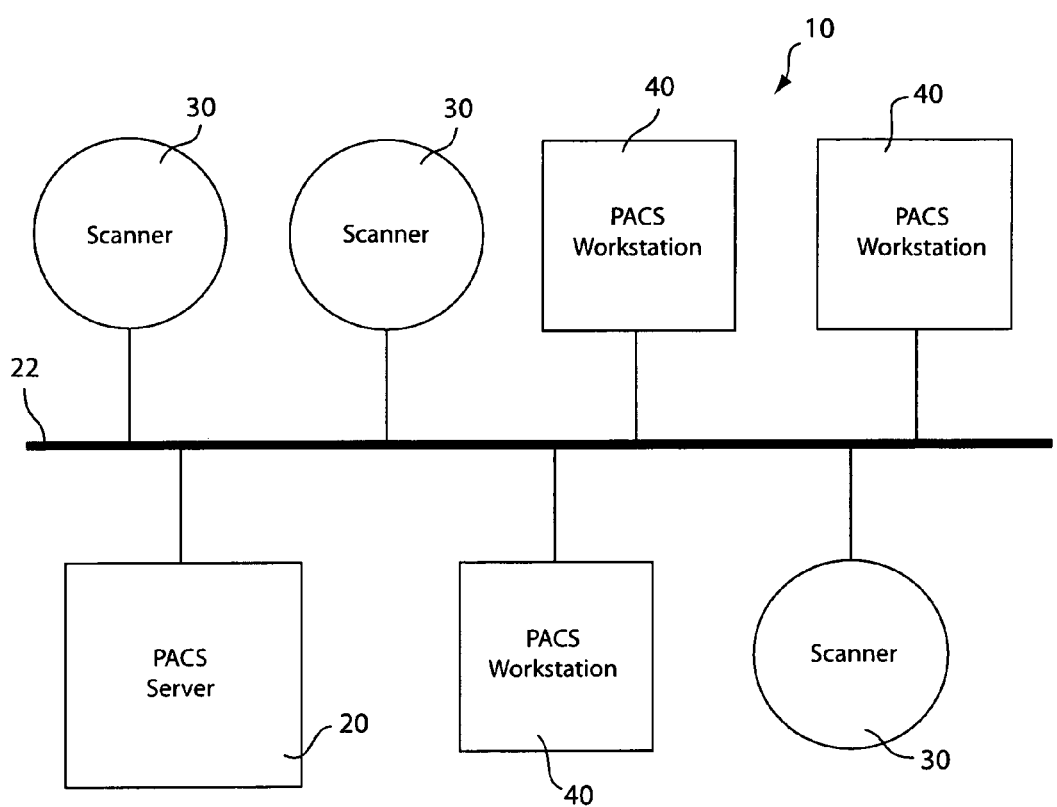
FIG. 1 is a block diagram of an image handling system.

Referring now to FIG. 1, a block diagram of an image handling system 10 is depicted. Image handling system 10 includes an image manager 20 which, in a preferred embodiment, is a picture archival and communication system (PACS) server, however image manager 20 is not limited to a PACS server, but may be any picture archiving apparatus. In a preferred embodiment, image manager 20 includes an information storage unit (ISU) for short-term storage and retrieval and an archival storage unit (e.g., an optical disc storage and optical disc reader system) for long-term storage and retrieval.

Image manager 20 is coupled to a plurality of imaging devices 30 which are configured to create digitized image information based on an image subject such as, but not limited to, portions of the human anatomy. In a preferred embodiment, imaging devices 30 include, but are not limited to magnetic resonance imaging (MRI) devices, ultrasound imaging devices, computed tomography (CT) devices, nuclear imaging devices, X-ray imaging devices and any other types of imaging devices, not limited to the medical field. In a preferred embodiment, imaging devices 30 produce image files in the DICOM3 or DEFF formats however, other image file formats are equally applicable. The image files are communicated from imaging devices 30 to image manager 20 as two dimensional slices or image information representative of two dimensional slices through the object being imaged. Therefore, from a single image file stored on image manager 20, a two dimensional image rendering may be reconstructed. Such two dimensional renderings are often presented to a user on any of a number of workstations 40 that are coupled to communications network 22 (such as an ethernet or other applicable communications network connection) that is in communication with image manager 20. Workstation 40 may be, in a preferred embodiment, a PACS workstation.

Figure 2:
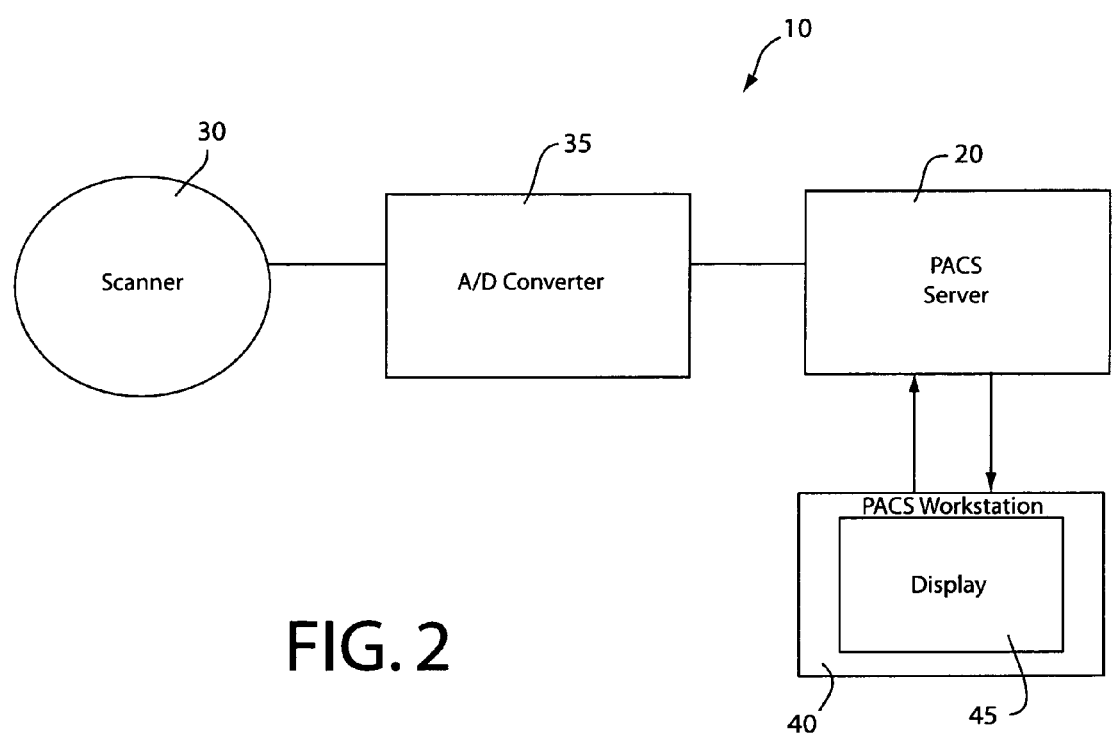
FIG. 2 is a block diagram of data flow from a scanning or imaging device to an imaging workstation.

In a preferred embodiment, it is preferable to have the option of viewing the imaged object in a three dimensional rendering on workstation 40 instead of a two dimensional rendering. Three dimensional renderings may be accomplished by a number of pertinent algorithms including surface rendering algorithms, maximum intensity projections (MIP) and other applicable three dimensional rendering processes. Referring now to FIG. 2, a block diagram, showing a portion of system 10, depicts the flow of information in system 10. In operation, scanner 30 scans an object, such as a patient. Scanner 30 generates an electrical signal representative of the configuration of the object. The analog signal is communicated to a digital analog converter 35. Digital analog converter 35 produces a digital signal that is communicated to PACS server or image manager 20. In an alternative embodiment, scanner 30 may directly generate a digital signal, thus digital to analog converter 35 would not be required. Further, alternatively scanner 30 may include the digital analog converter 35 therein. Image manager 20 stores the image signals in a file format such as DICOM3 or DEFF. The image files may be stored on any of a variety of storage devices, such as magnetic storage devices or optical storage devices. Image information from image manager 20 may be selectively retrieved by any of a number of workstations or other information retrieval devices coupled to communications network 22. Workstation 40 includes a display device 45.

To display a three dimensional image on display 45, workstation 40 may retrieve a plurality of two dimensional image files from image manager 20. However, in a preferred embodiment, workstation 40 includes programmed logic or software that allows display 45 to show a three dimensional image rendering that is generated on workstation 40. Further, in a preferred embodiment, the three dimensional image rendering (or parameters used to reconstruct the three dimensional image rendering) may be stored on the PACS workstation in a three dimensional image rendering file. The three dimensional rendering file may be communicated to and stored on the PACS server or image manager 20.

Therefore, a user working at a workstation 40 may retrieve three dimensional image rendering files that are stored on the PACS workstation 40 and have previously been generated on PACS workstation 40. The physician may manipulate (rotate, scale, colorize, measure, etc.) and view the three dimensional rendering, retrieved from the PACS workstation, that were previously generated by the PACS workstation and subsequently stored on the PACS workstation.

While the preferred embodiment refers to imaging devices used in the medical area, the reference to imaging devices may be interpreted broadly. The embodiment can encompass those situations in which any imaging device is coupled to and in communication with a communications network and an image manager.

Further, those who have skill in the art will recognize that the present invention is applicable with many different hardware configurations, software architectures, communications protocols and organizations or processes.

While the detailed drawings, specific examples, and particular formulations given describe preferred embodiments, they serve the purpose of illustration only. The materials and configurations shown and described may differ depending on the chosen performance characteristics and physical characteristics of the communications networks.

For example, the type of communications network or communications protocols used may differ. The systems shown and described are not limited to the precise details and conditions disclosed. Furthermore, other substitutions, modifications, changes, and omissions may be made in the design, operating conditions, and arrangements of the preferred embodiments without departing from the spirit of the invention as expressed in the appended claims.

The invention claimed is:

1. An image management system comprising:
a picture and archival and communication system (PACS) server having a plurality of inputs and outputs, the inputs configured to receive image information signals and the outputs configured to provide image output signals, the PACS server configured to store information representative of a plurality of two dimensional image slices in one of DICOM3 or DEFF format, and the output signals representative of the stored two dimensional image slices;
an imaging device having an output coupled to at least one of the inputs of the PACS server, and configured to provide an image signal; and
a PACS workstation having an input coupled to at least one of the outputs of the PACS server, and configured to receive output signals from the PACS server representative of selected two dimensional image slices stored by the PACS server, the PACS workstation configured to construct three dimensional image renderings from the two dimensional image slices by at least one of multi-plane reconstruction (MPR), multi-plane volume reconstruction (MPVR), and maximum intensity pixel (MIP) projection and the PACS workstation having an output coupled to the PACS server and configured to provide the PACS server with a signal representative of the three dimensional rendering.

2. The image management system of claim 1 wherein the three-dimensional rendering signal may be stored by the PACS server as a three-dimensional rendering file.

3. The image management system of claim 2 wherein the three-dimensional rendering file may be selectively communicated to a PACS workstation.

4. The image management system of claim 2 wherein the PACS server includes a three-dimensional rendering file storage.

5. The image management system of claim 2 wherein the three dimensional rendering file includes the parameters needed to reconstruct the three dimensional image rendering.

6. The image management system of claim 1 wherein the imaging device is a medical imaging device.

7. The image management system of claim 1 wherein the PACS workstation is configured to provide a three-dimensional rendering by volume rendering.

8. The image management system of claim 1 wherein the PACS workstation is configured to provide a three-dimensional rendering by surface rendering.

9. A method of producing a rendering of a three dimensional object from a plurality of two dimensional image information files, comprising:
receiving, by a picture archival and communication systems (PACS) server, a plurality of two dimensional image information files from an imaging device;
storing the plurality of two dimensional image information files on the PACS server in one of DICOM3 or DEFF format;
communicating selected two dimensional image information files to the PACS workstation;
receiving the selected two dimensional image information files by the PACS workstation;
constructing a three dimensional image information file based on the selected two dimensional image information files by at least one of multi-plane reconstruction (MPR), multi-plane volume reconstruction (MPVR), and maximum intensity pixel (MIP) projection; and
communicating the three dimensional image information file to the PACS server.

10. The method of claim 9 further comprising:
receiving a plurality of two dimensional image slices by the PACS workstation.

11. The method of claim 9 wherein the imaging device is a medical imaging device.

12. The method of claim 9 wherein the communicating step is carried out over an ethernet connection.

13. The method of claim 9 further comprising;
storing the three dimensional image file by the PACS server.

14. The method of claim 13 further comprising:
communicating the three dimensional image file stored by the PACS server to the PACS workstation.

15. The method claim 9 wherein the three dimensional image information file includes the parameters needed to reconstruct the three dimensional image rendering.

16. A medical imaging system, comprising:
a medical scanner,
a picture archival and communication system (PACS) server coupled to the medical scanner and configured to receive and store signals representative of two dimensional image slices from the medical scanner,
a PACS workstation configured to receive selected signals representative of two dimensional image slices and configured to construct a three dimensional rendering file from the signals representative of the two dimensional image slices,
wherein the three dimensional rendering file is communicated to and stored by the PACS server.

17. The medical imaging system of claim 16 wherein the medical scanner is an ultrasound imaging device.

18. The medical imaging system of claim 16 wherein the medical scanner is a magnetic resonance imaging (MRI) device.

19. The medical imaging system of claim 16 wherein the medical scanner is computed tomography (CT) imaging device.

20. The medical imaging system of claim 16 wherein the PACS workstation includes a display.

21. The medical imaging system of claim 20 wherein the PACS workstation is configured to provide a three dimensional rendering representative of the three dimensional rendering file on the display.

22. The medical imaging system of claim 16 wherein the three dimensional rendering file may be selectively communicated to the PACS workstation.

23. The medical imaging system of claim 16 wherein the three dimensional rendering file includes the parameters needed to reconstruct the three dimensional image rendering.

* * * * *